United States Patent
Kanno et al.

(10) Patent No.: US 9,206,106 B2
(45) Date of Patent: Dec. 8, 2015

(54) PRODUCTION METHOD OF CARBONYL COMPOUND

(71) Applicant: Kureha Corporation, Tokyo (JP)

(72) Inventors: Hisashi Kanno, Tokyo (JP); Toru Yamazaki, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 0 days.

(21) Appl. No.: 14/437,510

(22) PCT Filed: Oct. 2, 2013

(86) PCT No.: PCT/JP2013/076866
§ 371 (c)(1),
(2) Date: Apr. 22, 2015

(87) PCT Pub. No.: WO2014/083936
PCT Pub. Date: Jun. 5, 2014

(65) Prior Publication Data
US 2015/0299080 A1   Oct. 22, 2015

(30) Foreign Application Priority Data
Nov. 27, 2012  (JP) .................................. 2012-259166

(51) Int. Cl.
C07C 45/65   (2006.01)

(52) U.S. Cl.
CPC ....................................... C07C 45/65 (2013.01)

(58) Field of Classification Search
CPC ........................................................ C07C 45/65
USPC ........................................................ 568/346
See application file for complete search history.

(56) References Cited

U.S. PATENT DOCUMENTS

| | | | |
|---|---|---|---|
| 4,938,792 A | 7/1990 | Kumazawa et al. | |
| 5,481,029 A | 1/1996 | Braun et al. | |
| 6,642,418 B1 | 11/2003 | Cramp et al. | |

FOREIGN PATENT DOCUMENTS

| | | | |
|---|---|---|---|
| JP | 3-184838 A | 8/1991 | |
| JP | 3-184938 A | 8/1991 | |
| JP | 5-65243 A | 3/1993 | |
| JP | 5-78272 A | 3/1993 | |
| JP | H05271142 A | 10/1993 | |
| JP | H06157394 A | 6/1994 | |
| JP | H06321842 A | 11/1994 | |
| JP | 5-78262 A | 3/1995 | |
| JP | 2001048826 A | 2/2001 | |
| JP | 2002507586 A | 3/2002 | |
| JP | 2002371027 A | 12/2002 | |
| WO | WO/2011/070771 A1 | 6/2011 | |

OTHER PUBLICATIONS

International Search Report of PCT/JP2013/076865 dated Dec. 17, 2013.
International Preliminary Report on Patentability, and Translation of Written Opinion of the International Searching Authority, dated Jun. 11, 2015, for International Application No. PCT/JP2013/076866 (Forms PCT/IB/338, PCT/IB/373 and PCT/ISA/237).
International Search Report dated Dec. 17, 2013 for International Application No. PCT/JP2013/076866.
International Preliminary Report on Patentability, and Translation of Written Opinion of the International Searching Authority, dated Jun. 11, 2015, for International Application No. PCT/JP2013/076866 (Forms PCT/IB/338, PCT/IB/373 and PCT/ISA/237).

*Primary Examiner* — Sikarl Witherspoon
(74) *Attorney, Agent, or Firm* — Birch, Stewart, Kolasch & Birch, LLP

(57) ABSTRACT

The present invention is to provide a method of producing a carbonyl compound at a higher yield. The method of producing a carbonyl compound according to the present invention produces a carbonyl compound represented by general formula (I) by subjecting a compound represented by general formula (II) to dealkoxycarbonylation in the presence of a hydrogen halide salt of tertiary amine.

[Formula 1]

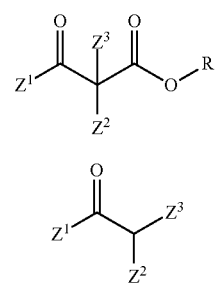

In the formula, R represents an alkyl group having from 1 to 4 carbons.

11 Claims, No Drawings

PRODUCTION METHOD OF CARBONYL COMPOUND

TECHNICAL FIELD

The present invention relates to a method of producing a carbonyl compound, and particularly relates to a method of producing a carbonyl compound by subjecting a -ketoester compound to dealkoxycarbonylation.

BACKGROUND ART

A certain type of 2-(halogenated hydrocarbon substituted)-5-benzyl-1-azolylmethylcyclopentanol derivative is described in Patent Document 1 as a compound that can be used as an active ingredient for agricultural and horticultural chemicals, industrial material protectants, and the like. A method of producing a 2-benzyl-5,5-bis(hydroxymethyl)-cyclopentanone derivative having a protected hydroxy group from a 1-benzyl-2-oxocyclopentane carboxylic acid alkyl ester derivative, which is a -ketoester compound, is also described in Patent Document 1 as a part of a step in the production method of this derivative.

CITATION LIST

Patent Literature

Patent Document 1: WO/2011/070771 (published Jun. 16, 2011)

SUMMARY OF INVENTION

Technical Problem

In order to produce a 2-(halogenated hydrocarbon substituted)-5-benzyl-1-azolylmethylcyclopentanol derivative, which is used as an active ingredient of agricultural and horticultural chemicals and the like, at lower cost and in a large quantity, the yield of a 2-benzyl-5,5-bis(hydroxymethyl)-cyclopentanone derivative having a protected hydroxy group needs to be enhanced.

The present invention is completed in the light of the problems described above. An object of the present invention is to provide a novel production method that can produce a carbonyl compound from -ketoester compound at a higher yield.

Solution to Problem

To solve the above-described problems, the method of producing a carbonyl compound according to the present invention is a method of producing a carbonyl compound represented by general formula (I) below from a compound represented by general formula (II) below, and the method comprises a step of subjecting the compound represented by general formula (II) below to dealkoxycarbonylation in the presence of a hydrogen halide salt of tertiary amine.

[Formula 1]

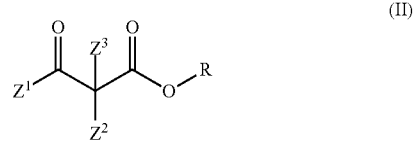

In general formula (II), $Z^1$ represents a substituted or unsubstituted alkyl group, cycloalkyl group, aryl group, or heterocyclic group; $Z^3$ and $Z^2$ each independently represent a hydrogen atom, a substituted or unsubstituted alkyl group, cycloalkyl group, aryl group, or heterocyclic group; and R represents an alkyl group having from 1 to 4 carbons. $Z^1$ and $Z^2$ may be bonded to each other.

[Formula 2]

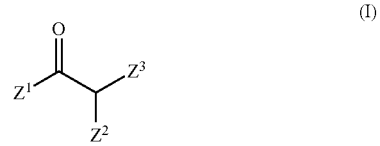

In general formula (I), $Z^1$, $Z^2$, and $Z^3$ are the same as $Z^1$, $Z^2$, and $Z^3$ in general formula (II) above, respectively.

Advantageous Effects of Invention

By the method of producing a carbonyl compound according to the present invention, a carbonyl compound can be produced at a high yield from a -ketoester compound.

DESCRIPTION OF EMBODIMENTS

As a result of diligent research, the present inventors have found that the yield of a 5-benzyl-2,2-bis(hydroxymethyl) cyclopentanone derivative having a protected hydroxy group can be enhanced by performing a reaction using a hydrogen halide salt of tertiary amine in a production step for obtaining a 5-benzyl-2,2-bis(hydroxymethyl)cyclopentanone derivative having a protected hydroxy group from a 1-benzyl-3,3-bis(hydroxymethyl)-2-oxocyclopentane carboxylic acid alkyl ester derivative having a protected hydroxy group. In addition, the present inventors have also found that a carbonyl compound can be produced at a high yield by using a hydrogen halide salt of tertiary amine in another reaction using another -ketoester compound. Therefore, the present invention has been completed.

An embodiment of the method of producing a carbonyl compound according to the present invention will be described hereinafter.

The method of producing a carbonyl compound according to the present invention is a method of producing a carbonyl compound represented by general formula (I) below from a -ketoester compound (hereinafter, referred to as "compound (II)") represented by general formula (II) below, and the method produces a carbonyl compound represented by general formula (I) by subjecting the compound (II) to dealkoxycarbonylation in the presence of a hydrogen halide salt of tertiary amine.

[Formula 3]

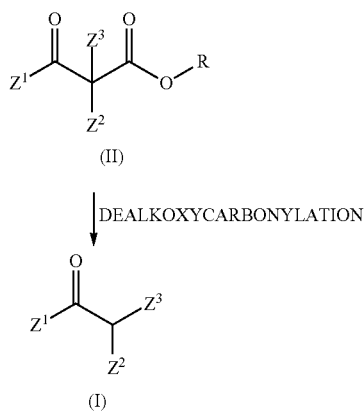

In the formula, $Z^1$ represents an alkyl group, cycloalkyl group, aryl group, or heterocyclic group, and the alkyl group, cycloalkyl group, aryl group, and heterocyclic group may have a substituent.

The number of carbons in alkyl group of $Z^1$ is not particularly limited; however, the alkyl group can be exemplified by an alkyl group having from 1 to 8 carbons. Examples of the alkyl group having from 1 to 8 carbons include an ethyl group, methyl group, (1-methyl)ethyl group, n-propyl group, 1-methylpropyl group, 2-methylpropyl group, 1,1-dimethylethyl group, n-butyl group, n-pentyl group, n-hexyl group, n-heptyl group, n-octyl group, and the like.

The number of carbons constituting the ring of the cycloalkyl group of $Z^1$ is not particularly limited; however, the cycloalkyl group can be exemplified by a cycloalkyl group having from 3 to 6 carbons. Examples of the cycloalkyl group having from 3 to 6 carbons include a cyclopropyl group, cyclobutyl group, cyclopentyl group, cyclohexyl group, and the like.

Examples of the aryl group of $Z^1$ include a phenyl group, naphthyl group, indene group, azulene group, diphenyl group, and the like.

The number of atoms constituting the ring of a heterocyclic group of $Z^1$ is not particularly limited; however, the heterocyclic group can be exemplified by an aliphatic heterocyclic group having from 3 to 6 members and an aromatic heterocyclic group having from 5 or 6 members. Examples of a heterocyclic ring constituting the aliphatic heterocyclic ring having from 3 to 6 members include azetidine, aziridine, piperidine, piperazine, morpholine, pyrrolidine, oxetane, tetrahydrofuran, tetrahydropyran, and the like. Furthermore, examples of a heterocyclic ring constituting the aromatic heterocyclic group having from 5 to 6 members include thiophene, pyridine, thiazole, furan, pyrrole, oxazole, isoxazole, isothiazole, triazole, furazan, imidazole, pyrazole, pyrazine, pyrimidine, triazine, pyridazine, and the like. Examples thereof also include condensed heterocyclic rings, such as indole, benzofuran, benzothiophene, quinoline, and quinoxaline; and the like.

Examples of the substituent that can be contained in the alkyl group, cycloalkyl group, aryl group, and heterocyclic group of $Z^1$ include a halogen atom, an aliphatic hydrocarbon group, an aromatic hydrocarbon group, an aromatic heterocyclic group, an aliphatic hydrocarbon group in which at least one hydrogen atom is substituted with an aromatic hydrocarbon group or aromatic heterocyclic group, an alkoxy group, a carbonyloxyalkyl group, an amide group, a cyano group, a nitro group, and the like. Furthermore, a hydrogen atom in these substituents may be substituted with a halogen atom, hydroxy group, alkoxy group, alkyl group, haloalkyl group, aromatic hydrocarbon group, aromatic heterocyclic group, and the like. Furthermore, the hydroxy group may be protected by a protecting group that protects the hydroxy group.

$Z^2$ and $Z^3$ each independently represent a hydrogen atom, alkyl group, cycloalkyl group, aryl group, or heterocyclic group, and the alkyl group, cycloalkyl group, aryl group, and heterocyclic group may have a substituent. Examples of the alkyl group, the cycloalkyl group, the aryl group, the heterocyclic group, and the substituent that can be contained in these alkyl group, cycloalkyl group, aryl group, and heterocyclic group of $Z^2$ and $Z^3$ are the same as the alkyl group, the cycloalkyl group, the aryl group, the heterocyclic group, and the substituent that can be contained in these alkyl group, cycloalkyl group, aryl group, and heterocyclic group of $Z^1$, respectively.

$Z^2$ and $Z^3$ may be the same or different from each other.

$Z^1$ and $Z^2$ may be bonded to each other and, together with a carbon atom to which $Z^1$ is bonded and a carbon atom to which $Z^2$ is bonded, form a ring.

R represents an alkyl group having from 1 to 4 carbons. Examples thereof include a methyl group, ethyl group, (1-methyl)ethyl group, n-propyl group, 1-methylpropyl group, 2-methylpropyl group, n-butyl group, 1,1-dimethylethyl group, and the like.

Examples of the tertiary amine constituting the hydrogen halide salt of tertiary amine include aliphatic amines such as trimethylamine, triethylamine, ethyldimethylamine, tri-n-propylamine, triisopropylamine, tri-n-butylamine, triisobutylamine, tri-sec-butylamine, tri-tert-butylamine, tri-n-pentylamine, tri-n-hexylamine, tri-n-octylamine, diethylisopropylamine, diisopropylethylamine, tricyclopropylamine, tricyclobutylamine, tetramethylethylene diamine, tricyclopentylamine, and tricyclohexylamine; nitrogen-containing heterocyclic aliphatic amines such as N-methylpyrrolidine, N-ethylpyrrolidine, N-methylpiperidine, N-ethylpiperidine, N-n-butylpiperidine, N-methylhexamethylene imine, N-ethylhexamethylene imine, N-methylmorpholine, N-ethylmorpholine, N-butylmorpholine, N,N'-dimethylpiperazine, N,N'-diethylpiperazine, 1,5-diazabicyclo[4.3.1]non-5-ene, 1,4-diazabicyclo[2.2.2]octane, and 1,8-diazabicyclo[5.4.0]undec-7-ene; and nitrogen-containing heterocyclic aromatic amines such as pyridine, picoline, collidine, and lutidine. Among these, triethylamine, trimethylamine, ethyldimethylamine, N-methylpyrrolidine, pyridine, and picoline are preferable; triethylamine, trimethylamine, pyridine, and picoline are more preferable; and triethylamine and pyridine are particularly preferable.

Examples of the hydrogen halide constituting the hydrogen halide salt of tertiary amine include hydrogen fluoride, hydrogen chloride, hydrogen bromide, and hydrogen iodide. Among these, hydrogen chloride is preferable.

Specific examples of preferable hydrogen halide salt of tertiary amine include a hydrochloride of triethylamine, triethylamine hydrobromide, trimethylamine hydrochloride, a hydrochloride of pyridine, 2-picoline hydrochloride, 3-picoline hydrochloride, and 4-picoline hydrochloride. Among these, a hydrochloride of triethylamine and a hydrochloride of pyridine are preferable.

Although a hydrogen halide salt of tertiary amine can be formed in a system by blowing a hydrogen halide, as a gas, into the system after adding tertiary amine into the system, it is preferable to use a hydrogen halide salt of tertiary amine that is prepared in advance.

The reaction of dealkoxycarbonylation is preferably performed in a solvent. The solvent is not particularly limited as long as the solvent does not participate in the reaction. For example, amides such as N,N-dimethylformamide, N,N-dimethylacetamide, and N-methyl-2-pyrrolidone can be preferably used. Furthermore, the solvent may be a mixed solvent with another solvent that can be mixed with these solvents (e.g. toluene, DMSO, and the like).

The amount of the hydrogen halide salt of tertiary amine is, in terms of moles, for example, from 0.3 to 10-fold, preferably from 0.5 to 5-fold, and more preferably from 0.8 to 3-fold, the amount of the compound (II).

The reaction temperature is, for example, from 0 to 250° C., preferably from room temperature to 200° C., and more preferably from 50 to 180° C. Furthermore, the reaction time is, for example, from 0.05 hours to a few days, preferably from 0.1 hours to 5 days, and more preferably from 0.5 hours to 2 days.

Note that, even when the reaction is not performed under inert gas, the reaction proceeds without problems. However, depending on the type of amine that is used, if the reaction takes place for a long time at a high temperature and if the reaction proceeds in the air, problems, such as coloration of the reaction liquid caused by being affected by air oxidation, may occur. In such a case, it is more preferable to perform the reaction under an inert gas (e.g. nitrogen, argon, and the like) atmosphere.

Other reaction conditions can be easily designed and set by a person skilled in the art by referring to conventionally known production methods.

In the present specification, "dealkoxycarbonylation" indicates that —$CO_2R$ is eventually substituted with a hydrogen atom. From the perspective of obtaining a carbonyl compound by removing —$CO_2R$ from a -ketoester compound, hydrolysis and decarboxylation of the -ketoester compound are the same. However, since, in the production method using a hydrogen halide salt of tertiary amine of the present invention, the reaction proceeds in the absence of water, the "dealkoxycarbonylation" in the present invention is clearly distinguished from a reaction including hydrolysis that requires water. Note that, if water is present in the reaction system, a hydroxide ion may be generated from the water molecule under a condition containing bases, thereby causing undesired side reactions. Therefore, it is preferred that the system contains no water.

In the production method according to the present invention, since the reaction is performed using a salt of tertiary amine, but not an acid or alkali, it is possible to perform the reaction under a neutral or almost neutral condition. Therefore, even for a compound which is unstable to an acid or alkali and the yield of which is anticipated to be lowered under acidic conditions or basic conditions, the reaction can be performed with a high yield.

The reaction mechanism of the dealkoxycarbonylation in the method of producing a carbonyl compound according to the present invention is conceived to include the following reaction mechanism, for example.

First, a halogen atom attacks an alkyl group of an alkyl ester group of the compound (II). As well as generating alkyl halide in the system, this forms -ketocarboxylic acid rapidly from the compound (II) since the hydrogen halide salt of tertiary amine is a proton source. Therefore, a compound represented by general formula (I) is formed by decarboxylation of the generated -ketocarboxylic acid. On the other hand, the generated alkyl halide reacts with the tertiary amine in the system to form a quaternary amine salt.

However, in the method of producing a carbonyl compound according to the present invention, the reaction mechanism is not particularly limited as long as the reaction proceeds using a hydrogen halide salt of tertiary amine. The method is not limited to cases where a single reaction mechanism proceeds the reaction, and the method may be a method where the reaction is proceeded by a plurality of reaction mechanisms.

A preferable aspect of the method of producing a carbonyl compound according to the present invention is a method of producing a carbonyl compound represented by general formula (Ia). The method produces a carbonyl compound represented by general formula (Ia) by subjecting a -ketoester compound having a cyclopentane ring represented by general formula (IIa) below (hereinafter, referred to as "compound (IIa)") to dealkoxycarbonylation in the presence of a hydrogen halide salt of tertiary amine.

[Formula 4]

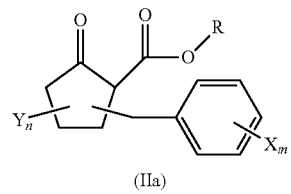

(IIa)

↓ DEALKOXYCARBONYLATION

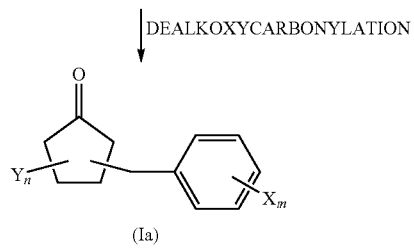

(Ia)

In the formula, Y represents an alkyl group or haloalkyl group having from 1 to 6 carbons, an alkenyl group or haloalkenyl group having from 2 to 6 carbons, an alkynyl group or haloalkynyl group having from 2 to 6 carbons, or a group in which a part of hydrogen atoms of the alkyl group, haloalkyl group, alkenyl group, haloalkenyl group, alkynyl group, or haloalkynyl group is substituted with —OG (G represents a protecting group of a hydroxy group).

Examples of the alkyl group having from 1 to 6 carbons include a methyl group, ethyl group, (1-methyl)ethyl group, n-propyl group, 1-methylpropyl group, 2-methylpropyl group, n-butyl group, 1-methylbutyl group, 2-methylbutyl group, 1-ethylpropyl group, 1,1-dimethylethyl group, and the like. Among these, alkyl groups having from 1 to 4 carbons are preferable. A methyl group and an ethyl group are more preferable, and a methyl group is even more preferable.

Examples of the haloalkyl group having from 1 to 6 carbons include a chloromethyl group, dichloromethyl group, trichloromethyl group, 2-chloroethyl group, 1-chloroethyl group, 2,2-dichloroethyl group, 1,2-dichloroethyl group, 2,2,2-trichloroethyl group, 3-chloropropyl group, 2,3-dichloropropyl group, 1-chloro-1-methylethyl group, 2-chloro-1-methylethyl group, 2-chloropropyl group, 4-chlorobutyl group, 5-chloropentyl group, fluoromethyl group, difluoromethyl group, trifluoromethyl group, 2-fluoroethyl group, 1-fluoroethyl group, 2,2-difluoroethyl group, 1,2-difluoroethyl group, 2,2,2-trifluoroethyl group, 3-fluoropropyl group, 2,3-difluoropropyl group, 1-fluoro-1-methylethyl group, 2-fluoro-1- methylethyl group, 2-fluoropropyl group, 3,3,3-trifluoropropyl group, 2,2,3,3-tetrafluoropropyl group, 2,2,3,3,3-pentafluoropropyl group, 4-fluorobutyl group, 5-fluoropentyl group, bromomethyl group, dibromomethyl group, tribromomethyl group, 2-bromoethyl group, 1-bromoethyl group, 2,2-dibromoethyl group, 1,2-dibromoethyl group, 2,2,2-tribromoethyl group, 3-bromopropyl group, 2,3-dibromopropyl group, 1-bromo-1-methylethyl group, 2-bromo-1-methylethyl group, 2-bromopropyl group, 4-bromobutyl group, 5-bromopentyl group, iodomethyl group, diiodomethyl group, 2-iodoethyl group, 1-iodoethyl group, 2,2-diiodoethyl group, 1,2-diiodoethyl group, 2,2,2-triiodoethyl group, 3-iodopropyl group, 2,3-diiodopropyl group, 1-iodo-1-methylethyl group, 2-iodo-1-methylethyl group, 2-iodopropyl group, 4-iodobutyl group, and the like. Among these, haloalkyl groups having from 1 to 4 carbons are preferable, and haloalkyl groups having from 1 to 3 carbons are more preferable.

Examples of the alkenyl group having from 2 to 6 carbons include an ethenyl group, 1,2-dimethylethenyl group, 4-methyl-1,3-butadienyl group, 1-propenyl group, 2-propenyl group, 2-methyl-2-propenyl group, 3-methyl-2-propenyl group, 2-butenyl group, 3-butenyl group, 3-methyl-3-butenyl group, and the like. Among these, alkenyl groups having from 2 to 4 carbons are preferable.

Examples of the haloalkenyl group having from 2 to 6 carbons include a 2-chloroethenyl group, 2,2-dichloroethenyl group, 2-chloro-2-propenyl group, 3,3-dichloro-2-propenyl group, 2,3-dichloro-2-propenyl group, 3,3-dichloro-2-methyl-2-propenyl group, 3-chloro-2-butenyl group, 2-fluoroethenyl group, 2,2-difluoroethenyl group, 2-fluoro-2-propenyl group, 3,3-difluoro-2-propenyl group, 2,3-difluoro-2-propenyl group, 3,3-difluoro-2-methyl-2-propenyl group, 3-fluoro-2-butenyl group, 2-bromoethenyl group, 2,2-dibromoethenyl group, 2-bromo-2-propenyl group, 3,3-dibromo-2-propenyl group, 2,3-dibromo-2-propenyl group, 3,3-dibromo-2-methyl-2-propenyl group, 3-bromo-2-butenyl group, 2-iodoethenyl group, 2,2-diiodoethenyl group, 2-iodo-2-propenyl group, 3,3-diiodo-2-propenyl group, 2,3-diiodo-2-propenyl group, and the like. Among these, haloalkenyl groups having from 2 to 4 carbons are preferable.

Examples of the alkynyl group having from 2 to 6 carbons include an ethynyl group, 1-propynyl group, 2-propynyl group, 1-butynyl group, 2-butynyl group, and the like. Among these, alkynyl groups having from 2 to 4 carbons are preferable.

Examples of the haloalkynyl group having from 2 to 6 carbons include a 2-fluoroethynyl group, 2-chloroethynyl group, 3-fluoro-2-propynyl group, 3-chloro-2-propynyl group, 3-bromo-2-propynyl group, and the like. Among these, haloalkynyl groups having from 2 to 4 carbons are preferable.

The protecting group G in —OG is a protecting group that protects a hydroxy group. The protecting group is not particularly limited as long as the protecting group dissociates under a proper condition to form a hydroxy group. Examples of the protecting group G include a protecting group that dissociates under acidic conditions, a protecting group that splits under reducing conditions such as a hydrogenation reaction, and the like.

n represents an integer from 0 to 6, and n is preferably from 0 to 3, and more preferably from 0 to 2. When n is 2 or greater, a plurality of Y may be the same or different each other. Furthermore, when n is 2 or greater, two Y moieties may be bonded to one carbon atom. Furthermore, when n is 2 or greater, a plurality of Y may be bonded to each other and, together with carbon atom(s) to which the plurality of Y are bonded, form a ring;

X represents a halogen atom, an alkyl group having from 1 to 4 carbons, a haloalkyl group having from 1 to 4 carbons, an alkoxy group having from 1 to 4 carbons, a haloalkoxy group having from 1 to 4 carbons, a phenyl group, a cyano group, or a nitro group.

Examples of the halogen atom of X include a fluorine atom, chlorine atom, bromine atom, iodine atom, and the like. Among these, a fluorine atom, chlorine atom, and bromine atom are preferable, and a fluorine atom and chlorine atom are more preferable.

Specific examples of the alkyl group having from 1 to 4 carbons of X include a methyl group, ethyl group, n-propyl group, isopropyl group, n-butyl group, isobutyl group, sec-butyl group, and tert-butyl group. Among these, alkyl groups having from 1 to 3 carbons are preferable. Alkyl groups having from 1 to 2 carbons are more preferable, and a methyl group is even more preferable.

Examples of the haloalkyl group having from 1 to 4 carbons of X include a dichloromethyl group, trichloromethyl group, 2-chloroethyl group, 1-chloroethyl group, 2,2-dichloroethyl group, 1,2-dichloroethyl group, 2,2,2-trichloroethyl group, 3-chloropropyl group, 2,3-dichloropropyl group, 1-chloro-1-methylethyl group, 2-chloro-1-methylethyl group, 2-chloropropyl group, 4-chlorobutyl group, fluoromethyl group, difluoromethyl group, trifluoromethyl group, 2-fluoroethyl group, 1-fluoroethyl group, 2,2-difluoroethyl group, 1,2-difluoroethyl group, 2,2,2-trifluoroethyl group, 3-fluoropropyl group, 2,3-difluoropropyl group, 1-fluoro-1-methylethyl group, 2-fluoro-1-methylethyl group, 2-fluoropropyl group, 3,3,3-trifluoropropyl group, 2,2,3,3-tetrafluoropropyl group, 2,2,3,3,3-pentafluoropropyl group, 4-fluorobutyl group, dibromomethyl group, tribromomethyl group, 2-bromoethyl group, 2,2-dibromoethyl group, 1,2-dibromoethyl group, 2,2,2-tribromoethyl group, 3-bromopropyl group, 2,3-dibromopropyl group, 1-bromo-1-methylethyl group, 2-bromo-1-methylethyl group, 2-bromopropyl group, diiodomethyl group, 2,2-diiodoethyl group, 1,2-diiodoethyl group, 2,2,2-triiodoethyl group, 2,3-diiodopropyl group, 1-iodo-1-methylethyl group, 2-iodo-1-methylethyl group, and the like. Among these, haloalkyl groups having from 1 to 3 carbons are preferable, and haloalkyl groups having 1 or 2 carbons are more preferable. Trihaloalkyl groups having 1 carbon are even more preferable.

Examples of the alkoxy group having from 1 to 4 carbons of X include a methoxy group, ethoxy group, n-propoxy group, and the like. Among these, alkoxy groups having from 1 to 3 carbons are preferable, and alkoxy groups having 1 or 2 carbons are more preferable. A methoxy group is even more preferable.

Examples of the haloalkoxy group having from 1 to 4 carbons of X include a trifluoromethoxy group, difluoromethoxy group, 1,1,2,2,2-pentafluoroethoxy group, 2,2,2-tifluoroethoxy group, and the like. Among these, haloalkoxy groups having from 1 to 3 carbons are preferable, and haloalkoxy groups having 1 or 2 carbons are more preferable. Dihalomethoxy groups and trihalomethoxy groups having 1 carbon are even more preferable.

m represents an integer from 0 to 5. m is preferably an integer from 0 to 3, more preferably an integer from 0 to 2, and even more preferably 0 or 1. When m is 2 or greater, a plurality of X may be the same or different each other. When m is 1 or greater, X may be positioned at any one of 2- to 6-positions of the benzene ring; however, when m is 1, X is preferably at a position that forms a 4-substituted benzyl.

R is the same as R in general formula (II) above.

The type and used amount of the hydrogen halide salt of tertiary amine and type of solvent used in the reaction that dealkoxycarbonylates the compound (IIa), reaction conditions of the reaction, and the like are the same as the above-described types and used amount of the hydrogen halide salt of tertiary amine, type of solvent, reaction conditions, and the like.

Preferable examples of the compound (IIa) include a compound represented by general formula (IIa-1) below and a compound represented by general formula (IIa-2) below.

[Formula 5]

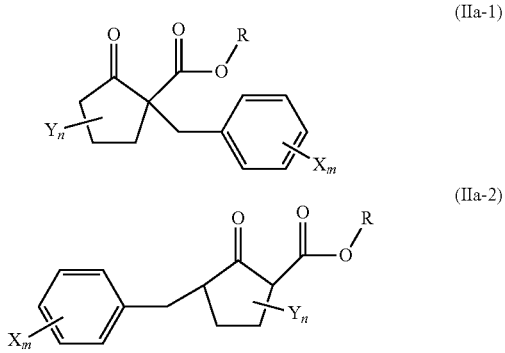

(IIa-1)

(IIa-2)

A more preferable aspect of the method of producing a carbonyl compound according to the present invention is a method of producing a carbonyl compound represented by general formula (Ib). The method produces a carbonyl compound represented by general formula (Ib) by subjecting a -ketoester compound having a cyclopentane ring represented by general formula (IIb) below (hereinafter, referred to as "compound (IIb)") to dealkoxycarbonylation in the presence of a hydrogen halide salt of tertiary amine.

[Formula 6]

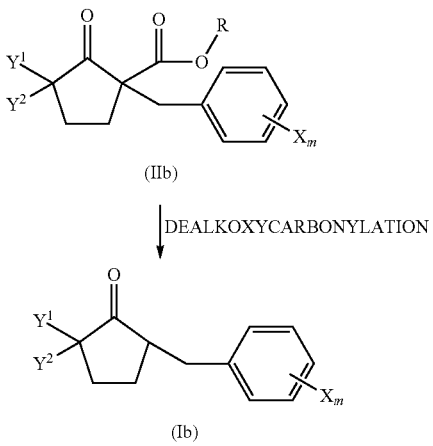

(IIb)

↓ DEALKOXYCARBONYLATION (Ib)

In the formula, $Y^1$ and $Y^2$ each independently represent an alkyl group or haloalkyl group having from 1 to 6 carbons, or a group in which a part of hydrogen atoms of the alkyl group or haloalkyl group is substituted with $—OG^1$ ($G^1$ represents a protecting group of a hydroxy group).

Examples of the alkyl group and haloalkyl group having from 1 to 6 carbons of $Y^1$ and $Y^2$ are the same as those for the alkyl group and haloalkyl group having from 1 to 6 carbons of Y described above.

$Y^1$ and $Y^2$ may be bonded to each other and, together with a carbon atom to which $Y^1$ and $Y^2$ are bonded, form a ring.

The protecting group $G^1$ is a protecting group that protects a hydroxy group. The protecting group is not particularly limited as long as the protecting group dissociates under a proper condition to form a hydroxy group. Examples of the protecting group $G^1$ include a protecting group that dissociates under acidic conditions. Examples of the protecting group that dissociates under acidic conditions include alkoxymethyl groups and alkoxyethyl groups in which alkoxy moiety has from 1 to 4 carbons (e.g. methoxymethyl group, ethoxymethyl group, and the like), alkyl groups having from 1 to 4 carbons (e.g. methyl group, ethyl group, t-butyl group, and the like), substituted or unsubstituted benzyl groups, substituted or unsubstituted tetrahydropyranyl groups, substituted or unsubstituted tetrahydrofuranyl groups, allyl groups, silyl groups (e.g. triethylsilyl group, t-butyldimethylsilyl group, and the like), and the like. Furthermore, the protecting groups for two hydroxy groups may be bonded to each other; for example, a case where two hydroxy groups are protected at the same time by an acetal, such as methylene acetal or ethylidene acetal, is possible.

Furthermore, examples thereof also include protecting groups that split under reducing conditions. Examples of the protecting group that splits under reducing conditions include a benzyl group, substituted or unsubstituted benzyl groups, such as a p-methoxybenzyl group, and the like.

Furthermore, R, X, and m are the same as R, X, and m in general formula (II) above.

The type and used amount of the hydrogen halide salt of tertiary amine and type of the solvent used in the reaction that dealkoxycarbonylates the compound (IIb), reaction conditions of the reaction, and the like are the same as the above-described types and used amount of the hydrogen halide salt of tertiary amine, type of solvent, reaction conditions, and the like.

Another preferable aspect of the method of producing a carbonyl compound according to the present invention is a method of producing a carbonyl compound represented by general formula (Ic) (hereinafter, referred to as "compound (Ic)"). The method produces a compound (Ic) by subjecting a -ketoester compound having a cyclopentane ring represented by general formula (IIc) below (hereinafter, referred to as "compound (IIc)") to dealkoxycarbonylation in the presence of a hydrogen halide salt of tertiary amine.

[Formula 7]

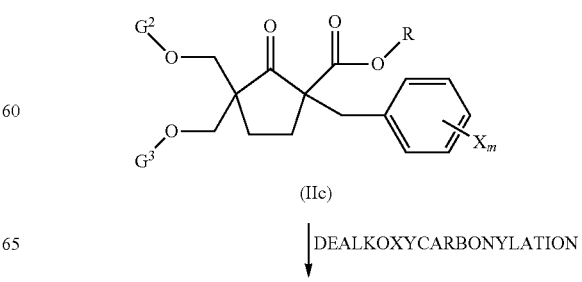

(IIc)

↓ DEALKOXYCARBONYLATION

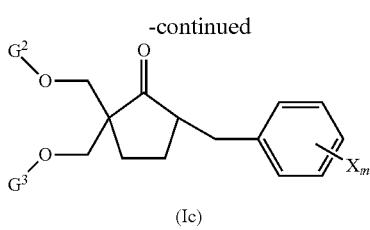

(Ic)

In the formula, $G^2$ and $G^3$ each independently represents a protective group that protects a hydroxy group, and, in particular, represents a protective group that dissociates under acidic conditions. Note that $G^2$ and $G^3$ may be bonded to each other and, together with oxygen atoms to which, respectively, $G^2$ and $G^3$ are bonded, carbon atoms to which, respectively, the oxygen atoms are bonded, and a carbon atom of the cyclopentane ring to which these carbon atoms are bonded, form a ring.

Examples of the protecting group for cases where $G^2$ and $G^3$ are not bonded to each other include alkoxymethyl groups in which alkoxy moiety has from 1 to 4 carbons (e.g. methoxymethyl group, ethoxymethyl group, and the like), alkoxyethyl groups in which alkoxy moiety has from 1 to 4 carbons (e.g. 1-ethoxyethyl group, 1-methyl-1-methoxyethyl group, and the like), alkyl groups having from 1 to 4 carbons (e.g. t-butyl group, methyl group, and the like), substituted or unsubstituted benzyl groups, substituted or unsubstituted tetrahydropyranyl groups, substituted or unsubstituted tetrahydrofuranyl groups, allyl groups, and silyl groups (e.g. triethylsilyl group, t-butyldimethylsilyl group, and the like).

On the other hand, examples of the protecting group for cases where $G^2$ and $G^3$ are bonded to each other include methylene acetal, ethylidene acetal, t-butylmethylidene ketal, 1-t-butylethylidene ketal, 1-phenylethylidene ketal, acrolein acetal, isopropylidene ketal (acetonide), cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene ketal, 2-nitrobenzylidene acetal, 4-nitrobenzylidene acetal, mesitylene acetal, 1-naphthaldehyde acetal, benzophenone ketal, camphor ketal, menthone ketal, methoxymethylene acetal, ethoxymethylene acetal, dimethoxymethylene orthoester, 1-methoxyethylidene orthoester, 1-ethoxyethylidene orthoester, methylidene orthoester, phthalide orthoester, 1,2-dimethoxyethylidene orthoester, □-methoxybenzylidene orthoester, 2-oxacyclopentylidene orthoester, butane-2,3-bis-acetal, cyclohexane-1,2-diacetal, bis-dihydropyran ketal, di-t-butylsilylene, 1,3-(1,1,3,3-tetraisopropyl)disiloxanilidene, and 1,1,3,3-tetra-t-butoxydisiloxanilidene.

Furthermore, R, X, and m are the same as R, X, and m in general formula (II) above.

The type and used amount of the hydrogen halide salt of tertiary amine and type of solvent used in the reaction that dealkoxycarbonylates the compound (IIc), reaction conditions of the reaction, and the like are the same as the above-described types and used amount of the hydrogen halide salt of tertiary amine, type of solvent, reaction conditions, and the like.

$G^2$ and $G^3$ are protecting groups that dissociate under acidic conditions. Therefore, for cases where hydrolysis and decarboxylation reactions are used in an attempt to obtain the compound (Ic) from the compound (IIc), the yield of the compound (Ic) decreases if the reaction is performed under acidic conditions. On the other hand, when the inventors of the present application conducted various investigations, it was found that, when the compound (IIc) was hydrolyzed/decarboxylated under basic conditions, the yield of the compound (Ic) decreased due to the occurrence of side reactions involving the opening of cyclopentane rings. Therefore, for a reaction to obtain the compound (Ic) from the compound (IIc), performing the reaction under a neutral or almost neutral condition is desired. According to the production method of the present invention in which dealkoxycarbonylation is performed using a hydrogen halide salt of tertiary amine, it is possible to perform the reaction under a neutral or almost neutral condition. Therefore, the production method of the present invention in which dealkoxycarbonylation is performed using a hydrogen halide salt of tertiary amine exhibits excellent effect especially in a method of producing the compound (Ic) from the compound (IIc) for which performing the reaction under a neutral or almost neutral condition is desired.

Furthermore, a side reaction in which a cyclopentane ring is opened upon performing hydrolysis/decarboxylation under basic conditions can occur not only in a reaction for the compound (IIc) but also in reactions for the compound (IIa) and the compound (IIb) in which a cyclopentane ring is contained. Therefore, when it is not desirable to perform hydrolysis/decarboxylation of the compound (IIa) and the compound (IIb) under acidic conditions due to some reasons (e.g. for cases where the yield will be decreased by performing hydrolysis/decarboxylation under acidic conditions), the production method of the present invention in which dealkoxycarbonylation is performed using a hydrogen halide salt of tertiary amine is particularly preferably employed.

Since the hydrogen halide salt of tertiary amine is an acid of strong acid and weak base, the reaction system may be acidic. Therefore, when the production method of the present invention is applied to a compound, the yield of which is expected to be lowered by a reaction under acidic conditions, such as the compound (IIc) and a compound represented by general formula (IId) or (IIe) described below having a protecting group that dissociates under acidic conditions, a base is preferably added to the reaction system. By adding a base in the reaction system, decrease in the yield of the target product can be prevented. Examples of a base to be added include tertiary amines. Note that a tertiary amine that is added as a base may be the same as or different from the tertiary amine that constitutes the hydrogen halide salt of tertiary amine used in the reaction. However, it is preferable to use a tertiary amine that is the same as the tertiary amine used in the reaction.

For cases where a base is added, the added amount of the base may be suitably set depending on the type and used amount of the hydrogen halide salt of tertiary amine and type of the added base. However, for example, for cases where a tertiary amine that is the same as the tertiary amine used in the hydrogen halide salt of tertiary amine is added as a base, the amount of the base may be, in terms of moles, for example, from 0.01 to 2-fold, preferably from 0.05 to 1-fold, more preferably from 0.1 to 0.5-fold, the amount of the hydrogen halide salt of tertiary amine A preferable aspect for cases where $G^2$ and $G^3$ are bonded to each other to form a ring is a method of producing a carbonyl compound represented by general formula (Id). The method produces a carbonyl compound represented by general formula (Id) by subjecting a -ketoester compound having a cyclopentane ring represented by general formula (IId) below to dealkoxycarbonylation in the presence of a hydrogen halide salt of tertiary amine.

[Formula 8]

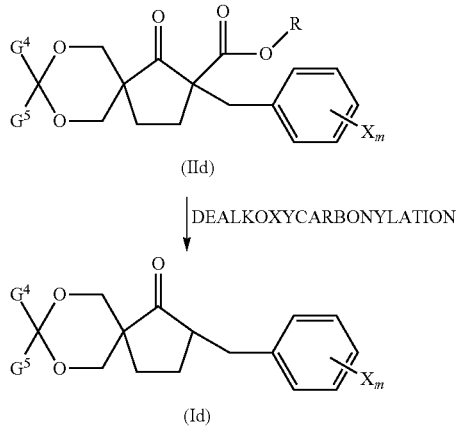

(IId)

↓ DEALKOXYCARBONYLATION (Id)

In the formula, $G^4$ and $G^5$ each independently represent a hydrogen atom, an alkyl group having from 1 to 4 carbons, an alkenyl group having from 1 to 4 carbons, a phenyl group, a naphthyl group, or a benzyl group. A phenyl moiety of the phenyl group, naphthyl group, and benzyl group of $G^4$ and $G^5$ may be substituted with an alkyl group having from 1 to 4 carbons (e.g. methyl group, ethyl group, and the like); an alkoxy group having from 1 to 4 carbons (e.g. methoxy group, ethoxy group, and the like); a nitro group; or a halogen atom (e.g. fluorine atom, chlorine atom, and the like). Note that $G^4$ and $G^5$ may be bonded to each other and, together with a carbon atom to which $G^4$ and $G^5$ are bonded, form a ring. Among these, $G^4$ and $G^5$ are more preferably each independently a hydrogen atom or an alkyl group having from 1 to 4 carbons, such as a methyl group, ethyl group, and n-propyl group; and even more preferably each independently a hydrogen atom, methyl group, or ethyl group. Furthermore, both of $G^4$ and $G^5$ are particularly preferably methyl groups.

Furthermore, R, X, and m are the same as R, X, and m in general formula (II) above.

The type and used amount of the hydrogen halide salt of tertiary amine and type of solvent used in the reaction that dealkoxycarbonylates the -ketoester compound represented by general formula (IId), reaction conditions of the reaction, and the like are the same as the above-described types and used amount of the hydrogen halide salt of tertiary amine, type of solvent, reaction conditions, and the like.

A particularly preferable aspect of the method of producing a carbonyl compound according to the present invention is a method of producing a carbonyl compound represented by general formula (Ie). The method produces a carbonyl compound represented by general formula (Ie) by subjecting a -ketoester compound having a cyclopentane ring represented by general formula (IIe) below to dealkoxycarbonylation in the presence of a hydrogen halide salt of tertiary amine

[Formula 9]

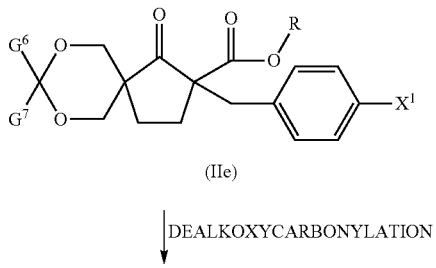

(IIe)

↓ DEALKOXYCARBONYLATION

-continued

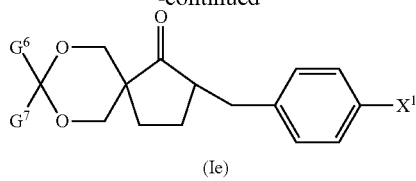

(Ie)

In the formula, $G^6$ and $G^7$ each independently represent a hydrogen atom or an alkyl group having from 1 to 4 carbons, such as a methyl group, ethyl group, and n-propyl group. Among these, $G^6$ and $G^7$ are preferably each independently a hydrogen atom, methyl group, or ethyl group. Furthermore, both of $G^6$ and $G^7$ are more preferably methyl groups.

$X^1$ represents a hydrogen atom, chlorine atom, or fluorine atom.

SUMMARY

To solve the above-described problems, the method of producing a carbonyl compound according to the present invention is a method of producing a carbonyl compound represented by general formula (I) below from a compound represented by general formula (II) below, and the method comprises a step of subjecting the compound represented by general formula (II) below to dealkoxycarbonylation in the presence of a hydrogen halide salt of tertiary amine.

[Formula 10]

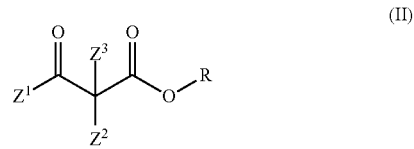

(II)

In general formula (II), $Z^1$ represents a substituted or unsubstituted alkyl group, cycloalkyl group, aryl group, or heterocyclic group; $Z^3$ and $Z^2$ each independently represent a hydrogen atom, a substituted or unsubstituted alkyl group, cycloalkyl group, aryl group, or heterocyclic group; and R represents an alkyl group having from 1 to 4 carbons. $Z^1$ and $Z^2$ may be bonded to each other.

[Formula 11]

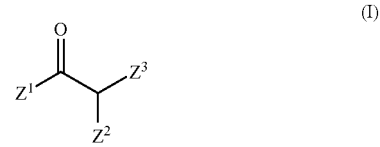

(I)

In general formula (I), $Z^1$, $Z^2$, and $Z^3$ are the same as $Z^1$, $Z^2$, and $Z^3$ in general formula (II) above, respectively.

Furthermore, in the method of producing a carbonyl compound according to the present invention, a tertiary amine constituting the hydrogen halide salt of tertiary amine is preferably triethylamine, trimethylamine, pyridine, or picoline.

Furthermore, in the method of producing a carbonyl compound according to the present invention, the hydrogen halide salt of tertiary amine is preferably a hydrochloride of tertiary amine or a hydrobromide of tertiary amine.

Furthermore, in the method of producing a carbonyl compound according to the present invention, the compound represented by general formula (II) above is preferably a compound represented by general formula (IIa) below; and the carbonyl compound represented by general formula (I) above is preferably a carbonyl compound represented by general formula (Ia) below:

[Formula 12]

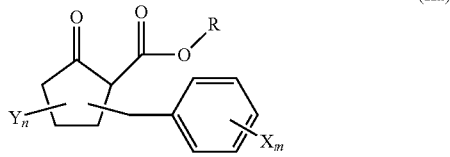

(IIa)

In general formula (IIa), R represents an alkyl group having from 1 to 4 carbons, Y represents an alkyl group or haloalkyl group having from 1 to 6 carbons, an alkenyl group or haloalkenyl group having from 2 to 6 carbons, an alkynyl group or haloalkynyl group having from 2 to 6 carbons, or a group in which a part of hydrogen atoms of the alkyl group, haloalkyl group, alkenyl group, haloalkenyl group, alkynyl group, or haloalkynyl group is substituted with —OG (G represents a protecting group of a hydroxy group); and n is an integer from 0 to 6. When n is 2 or greater, a plurality of Y may be the same or different. When n is 2 or greater, a plurality of Y may be bonded to each other and, together with carbon atom(s) to which the plurality of Y are bonded, form a ring. X represents a halogen atom, an alkyl group having from 1 to 4 carbons, a haloalkyl group having from 1 to 4 carbons, an alkoxy group having from 1 to 4 carbons, a haloalkoxy group having from 1 to 4 carbons, a phenyl group, a cyano group, or a nitro group; and m is an integer from 0 to 5, when m is 2 or greater, a plurality of X may be the same or different.

[Formula 13]

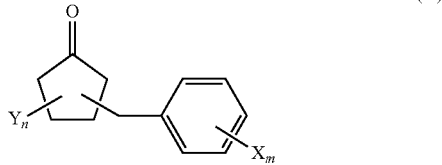

(Ia)

In general formula (Ia), X, Y, m, and n are the same as X, Y, m, and n in general formula (IIa) above, respectively.

Furthermore, in the method of producing a carbonyl compound according to the present invention, the compound represented by general formula (IIa) above is preferably a compound represented by general formula (IIb) below; and the carbonyl compound represented by general formula (Ia) above is preferably a carbonyl compound represented by general formula (Ib) below:

[Formula 14]

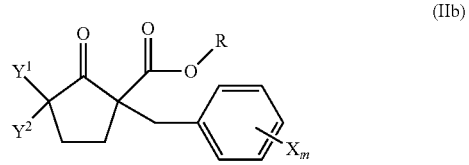

(IIb)

In general formula (IIb), $Y^1$ and $Y^2$ each independently represent an alkyl group or haloalkyl group having from 1 to 6 carbons, or a group in which a part of hydrogen atoms of the alkyl group or haloalkyl group is substituted with —$OG^1$ ($G^1$ represents a protecting group of a hydroxy group), and $Y^1$ and $Y^2$ may be bonded to each other and, together with a carbon atom to which $Y^1$ and $Y^2$ are bonded, form a ring. R, X, and m are the same as R, X, and m in general formula (IIa) above, respectively.

[Formula 15]

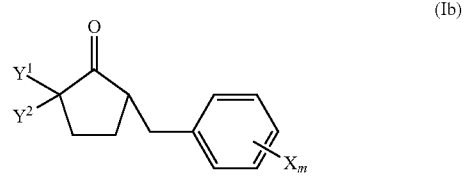

(Ib)

In general formula (Ib), X, $Y^1$, $Y^2$, and m are the same as X, $Y^1$, $Y^2$, and m in general formula (IIb) above, respectively.

Furthermore, in the method of producing a carbonyl compound according to the present invention, the compound represented by general formula (IIb) above is preferably a compound represented by general formula (IIc) below; and the carbonyl compound represented by general formula (Ib) above is preferably a carbonyl compound represented by general formula (Ic) below:

[Formula 16]

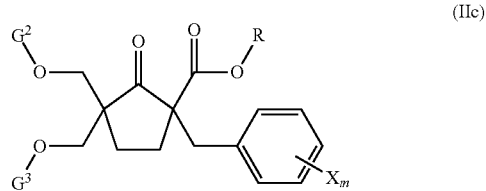

(IIc)

In general formula (IIc), $G^2$ and $G^3$ each independently represent a protecting group that dissociates under acidic conditions, and $G^2$ and $G^3$ may be bonded to each other. R, X, and m are the same as R, X, and m in general formula (IIa) above, respectively.

[Formula 17]

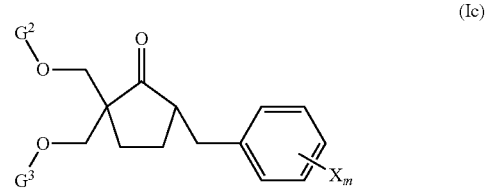

(Ic)

In general formula (Ic), X, $G^2$, $G^3$, and m are the same as X, $G^2$, $G^3$, and m in general formula (IIc) above, respectively.

Furthermore, in the method of producing a carbonyl compound according to the present invention, the compound represented by general formula (IIc) above is preferably a compound represented by general formula (IId) below; and the carbonyl compound represented by general formula (Ic) above is preferably a carbonyl compound represented by general formula (Id) below:

[Formula 18]

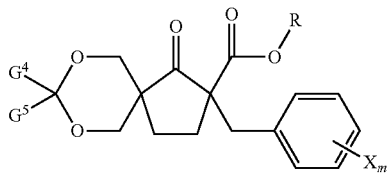

(IId)

In general formula (IId), $G^4$ and $G^5$ each independently represent a hydrogen atom, an alkyl group having from 1 to 4 carbons, an alkenyl group having from 1 to 4 carbons, a substituted or unsubstituted phenyl group, naphthyl group, or benzyl group, and $G^4$ and $G^5$ may be bonded to each other and, together with a carbon atom to which $G^4$ and $G^5$ are bonded, form a ring. R, X, and m are the same as R, X, and m in general formula (IIa) above, respectively.

[Formula 19]

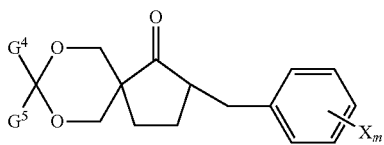

(Id)

In general formula (Id), X, $G^4$, $G^5$, and m are the same as X, $G^4$, $G^5$, and m in general formula (IId) above, respectively.

Furthermore, in the method of producing a carbonyl compound according to the present invention, $G^4$ and $G^5$ are preferably each independently a hydrogen atom or an alkyl group having from 1 to 4 carbons.

Furthermore, in the method of producing a carbonyl compound according to the present invention, a tertiary amine is preferably further added to the reaction system.

Furthermore, in the method of producing a carbonyl compound according to the present invention, m is preferably an integer from 0 to 2; and when m is 1 or 2, X is preferably a halogen atom.

Embodiments of the present invention will be described in more detail hereinafter using examples. Of course, the present invention is not limited to the examples below, and it goes without saying that various modes are possible with regard to the details thereof. Furthermore, the present invention is not limited to the embodiments described above, and various modifications are possible within the scope indicated in the claims. Embodiments obtained by appropriately combining the technical means disclosed by the embodiments are also included in the technical scope of the present invention. In addition, all of the documents disclosed in the present specification are hereby incorporated by reference.

EXAMPLES

Working Example 1

Synthesis of 5-(4-chlorobenzyl)-2,2-bis((methoxymethoxy)methyl)cyclopentanone

In 1-(4-chlorobenzyl)-3,3-bis((methoxymethoxy)methyl)-2-oxocyclopentane carboxylic acid methyl ester (2.0 g, 0.00482 mol), N,N-dimethylacetamide (2 mL), triethylamine (0.20 mL, 0.00482×0.3 mol), and triethylamine hydrochloride (0.995 g, 0.0482×1.5 mol) were added and stirred at 130° C. for 8 hours. In the reaction liquid, ethyl acetate and saturated sodium bicarbonate water were added, and the mixture was partitioned. After extracting the aqueous layer using ethyl acetate, the organic layer was dried using anhydrous sodium sulfate and concentrated. Thereafter, the dried and concentrated product was purified using a silica gel column, and a target product was obtained.

The yield in grams was 1.51 g, and the percent yield was 88%.

Working Example 2

Synthesis of 2-(4-chlorobenzyl)-8,8-dimethyl-7,9-dioxaspiro[4.5]decan-1-one

In 2-(4-chlorobenzyl)-8,8-dimethyl-1-oxo-7,9-dioxaspiro[4.5]decane-2-carboxylic acid methyl ester (2.0 g, 0.00546 mol), N,N-dimethylacetamide (2 mL), triethylamine (0.20 mL, 0.00546×0.3 mol), and triethylamine hydrochloride (1.13 g, 0.0546×1.5 mol) were added and stirred at 155° C. for 1.5 hours. In the reaction liquid, toluene and saturated sodium bicarbonate water were added, and the mixture was partitioned. After extracting the aqueous layer using toluene, the organic layer was dried using anhydrous sodium sulfate and concentrated. Thereafter, the dried and concentrated product was purified using a silica gel column, and a target product was obtained.

The yield in grams was 1.62 g, and the percent yield was 96%.

Working Example 3

Synthesis of 2-(4-chlorobenzyl)-7,9-dioxaspiro[4.5]decan-1-one

In 2-(4-chlorobenzyl)-1-oxo-7,9-dioxaspiro[4.5]decane-2-carboxylic acid methyl ester (4.0 g, 0.0118 mol), N,N-dimethylacetamide (4 mL), triethylamine (0.15 mL, 0.0118×0.1 mol), and triethylamine hydrochloride (1.79 g, 0.0118×1.1 mol) were added and stirred at 120° C. for 4 hours. In the reaction liquid, toluene and saturated sodium bicarbonate water were added, and the mixture was partitioned. After extracting the aqueous layer using toluene, the organic layer was dried using anhydrous sodium sulfate and concentrated. Thereafter, the dried and concentrated product was purified using a silica gel column, and a target product was obtained.

The yield in grams was 2.92 g, and the percent yield was 88%.

Working Example 4

Synthesis 1 of 5-(4-chlorobenzyl)-2,2-dimethyl cyclopentanone

In 1-(4-chlorobenzyl)-3,3-dimethyl-2-oxocyclopentane carboxylic acid methyl ester (1.5 g, 0.00509 mol), N,N-dimethylacetamide (1.5 mL) and pyridine hydrochloride (0.706 g, 0.00509×1.2 mol) were added and stirred at 155° C. for 4 hours. In the reaction liquid, pyridine hydrochloride (0.177 g, 0.00509×0.3 mol) was added and further stirred at 155° C. for another 6 hours. In the reaction liquid, toluene and saturated sodium bicarbonate water were added, and the mixture was partitioned. After extracting the aqueous layer using toluene, the organic layer was dried using anhydrous sodium sulfate and concentrated. Thereafter, the dried and concentrated product was purified using a silica gel column, and a target product was obtained.

The yield in grams was 1.08 g, and the percent yield was 90%.

Working Example 5

Synthesis 2 of 5-(4-chlorobenzyl)-2,2-dimethyl cyclopentanone

In 1-(4-chlorobenzyl)-3,3-dimethyl-2-oxocyclopentane carboxylic acid methyl ester (1.0 g, 0.00339 mol), N,N-dimethylacetamide (1 mL) and triethylamine hydrochloride (0.56 g, 0.00339×1.2 mol) were added and stirred at 150° C. for 2 hours. In the reaction liquid, toluene and saturated sodium bicarbonate water were added, and the mixture was partitioned. After extracting the aqueous layer using toluene, the organic layer was dried using anhydrous sodium sulfate and concentrated. Thereafter, the dried and concentrated product was purified using a silica gel column, and a target product was obtained.

The yield in grams was 0.745 g, and the percent yield was 93%.

Working Example 6

Synthesis of 2-(4-chlorobenzyl)cyclopentanone

In 3-(4-chlorobenzyl)-2-oxocyclopentane carboxylic acid methyl ester (1.0 g, 0.00375 mol), N,N-dimethylacetamide (1 mL) and triethylamine hydrochloride (0.774 g, 0.00375×1.5 mol) were added and stirred at 130° C. for 2 hours, and then at 140° C. for another 3 hours. In the reaction liquid, ethyl acetate and saturated sodium bicarbonate water were added, and the mixture was partitioned. After extracting the aqueous layer using ethyl acetate, the organic layer was dried using anhydrous sodium sulfate and concentrated. Thereafter, the dried and concentrated product was purified using a silica gel column, and a target product was obtained.

The yield in grams was 0.71 g, and the percent yield was 91%.

Working Example 7

Synthesis of 1-(4-chlorophenyl)ethanone

In 3-(4-chlorophenyl)-3-oxopropionic acid methyl ester (1.0 g, 0.0047 mol), N,N-dimethylacetamide (1 mL) and triethylamine hydrochloride (0.97 g, 0.0047×1.5 mol) were added and stirred at 140° C. for 3 hours under an argon atmosphere. In the reaction liquid, ethyl acetate and saturated sodium bicarbonate water were added, and the mixture was partitioned. After extracting the aqueous layer using ethyl acetate, the organic layer was dried using anhydrous sodium sulfate and concentrated. Thereafter, the dried and concentrated product was purified using a silica gel column, and a target product was obtained.

The yield in grams was 0.688 g, and the percent yield was 95%.

Comparative Example 1

Synthesis of 5-(4-chlorobenzyl)-2,2-bis((methoxymethoxy)methyl)cyclopentanone

In isopropanol (5.5 mL), 1-(4-chlorobenzyl)-3,3-bis((methoxymethoxy)methyl)-2-oxocyclopentane carboxylic acid methyl ester (2.2895 g, 5.52 mmol) was dissolved, and a 2 M sodium hydroxide solution (5.5 mL) was added thereto. The mixture was stirred at 90° C. for 2 hours. Following the completion of the reaction, water was added, and the mixture was subjected to extraction using ethyl acetate. The organic layer was washed with saturated brine solution and water, and dried using anhydrous sodium sulfate. The solvent was distilled out, and the residue was purified using silica gel to obtain a target product.

The yield in grams was 1.3029 g, and the percent yield was 66%.

Reference Example 1

Synthesis 1 of 2-(4-chlorobenzyl)-8,8-dimethyl-7,9-dioxaspiro[4.5]decan-1-one

After adding toluene (1 mL) in 2-(4-chlorobenzyl)-8,8-dimethyl-1-oxo-7,9-dioxaspiro[4.5]decane-2-carboxylic acid methyl ester (10.0 g, 0.0273 mol), the mixture was suspended in a 0.5 M sodium hydroxide solution (27.3 mL, 0.0273 mol×0.5 mol) and reacted at 110° C. The reaction was continued by adding a 0.5 M sodium hydroxide solution (27.3 mL, 0.0273 mol×0.5 mol) every 2 hours (for three times total), and heating and stirring were performed for total of 9 hours. Following the completion of the reaction, the mixture was allowed to cool to room temperature and then subjected to extraction using toluene. The organic layer was washed with saturated brine solution, and then dried using anhydrous sodium sulfate. Thereafter, the dried product was purified using a silica gel column, and a target product was obtained.

The yield in grams was 6.75 g, and the percent yield was 80%.

INDUSTRIAL APPLICABILITY

The present invention can be used in the production of a 2-benzyl-5,5-di(protected hydroxymethyl)-cyclopentanone derivative serving as a raw material for an agricultural chemical or the like.

The invention claimed is:

1. A method of producing a carbonyl compound represented by general formula (I) below from a compound represented by general formula (II) below;

the method comprising a step of: subjecting the compound represented by general formula (II) below to dealkoxycarbonylation in the presence of a hydrogen halide salt of tertiary amine:

[Formula 1]

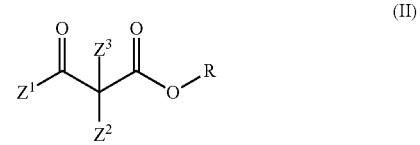

(II)

wherein, in general formula (II), $Z^1$ represents a substituted or unsubstituted alkyl group, cycloalkyl group, aryl group, or heterocyclic group; $Z^3$ and $Z^2$ each independently represent a hydrogen atom, a substituted or unsubstituted alkyl group, cycloalkyl group, aryl group, or heterocyclic group; R represents an alkyl group having from 1 to 4 carbons; and $Z^1$ and $Z^2$ may be bonded to each other; and

[Formula 2]

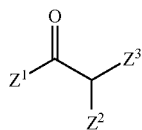

(I)

wherein, in general formula (I), $Z^1$, $Z^2$, and $Z^3$ are the same as $Z^1$, $Z^2$, and $Z^3$ in general formula (II) above, respectively.

2. The method of producing a carbonyl compound according to claim 1, wherein a tertiary amine constituting the hydrogen halide salt of tertiary amine is triethylamine, trimethylamine, pyridine, or picoline.

3. The method of producing a carbonyl compound according to claim 1, wherein the hydrogen halide salt of tertiary amine is a hydrochloride of tertiary amine or a hydrobromide of tertiary amine.

4. The method of producing a carbonyl compound according to claim 1, wherein the hydrogen halide salt of tertiary amine is a hydrochloride of triethylamine or a hydrochloride of pyridine.

5. The method of producing a carbonyl compound according to claim 1, wherein the compound represented by general formula (II) above is a compound represented by general formula (IIa) below; and the carbonyl compound represented by general formula (I) above is a carbonyl compound represented by general formula (Ia) below:

[Formula 3]

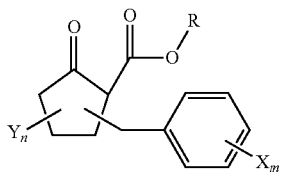

(IIa)

wherein, in general formula (IIa), R represents an alkyl group having from 1 to 4 carbons, Y represents an alkyl group or haloalkyl group having from 1 to 6 carbons, an alkenyl group or haloalkenyl group having from 2 to 6 carbons, an alkynyl group or haloalkynyl group having from 2 to 6 carbons, or a group in which a part of hydrogen atoms of the alkyl group, haloalkyl group, alkenyl group, haloalkenyl group, alkynyl group, or haloalkynyl group is substituted with —OG (G represents a protecting group of a hydroxy group); n is an integer from 0 to 6, when n is 2 or greater, a plurality of Y may be the same or different, when n is 2 or greater, a plurality of Y may be bonded to each other and, together with a carbon atom to which the plurality of Y are bonded, form a ring; X represents a halogen atom, an alkyl group having from 1 to 4 carbons, a haloalkyl group having from 1 to 4 carbons, an alkoxy group having from 1 to 4 carbons, a haloalkoxy group having from 1 to 4 carbons, a phenyl group, a cyano group, or a nitro group; and m is an integer from 0 to 5, when m is 2 or greater, a plurality of X may be the same or different; and

[Formula 4]

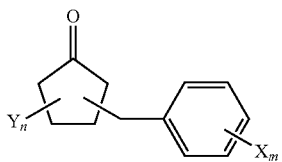

(Ia)

wherein, in general formula (Ia), X, Y, m, and n are the same as X, Y, m, and n in general formula (IIa) above, respectively.

6. The method of producing a carbonyl compound according to claim 5, wherein the compound represented by general formula (IIa) above is a compound represented by general formula (IIb) below; and the carbonyl compound represented by general formula (Ia) above is a carbonyl compound represented by general formula (Ib) below:

[Formula 5]

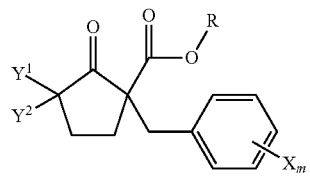

(IIb)

wherein, in general formula (IIb), $Y^1$ and $Y^2$ each independently represent an alkyl group or haloalkyl group having from 1 to 6 carbons, or a group in which a part of hydrogen atoms of the alkyl group or haloalkyl group is substituted with —$OG^1$ ($G^1$ represents a protecting group of a hydroxy group), $Y^1$ and $Y^2$ may be bonded to each other and, together with a carbon atom to which $Y^1$ and $Y^2$ are bonded, form a ring; and R, X, and m are the same as R, X, and m in general formula (IIa) above, respectively; and

[Formula 6]

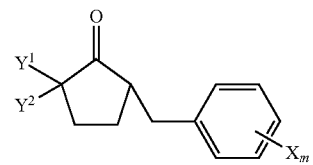

(Ib)

wherein, in general formula (Ib), X, $Y^1$, $Y^2$, and m are the same as X, $Y^1$, $Y^2$, and m in general formula (IIb) above, respectively.

7. The method of producing a carbonyl compound according to claim 6, wherein the compound represented by general formula (IIb) above is a compound represented by general formula (IIc) below; and the carbonyl compound represented by general formula (Ib) above is a carbonyl compound represented by general formula (Ic) below:

[Formula 7]

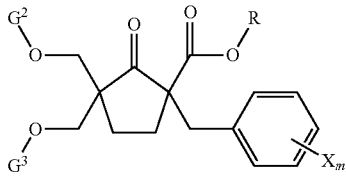

(IIc)

wherein, in general formula (IIc), $G^2$ and $G^3$ each independently represent a protecting group that dissociates under an acidic condition, and $G^2$ and $G^3$ may be bonded to each other; and R, X, and m are the same as R, X, and m in general formula (IIa) above, respectively; and

[Formula 8]

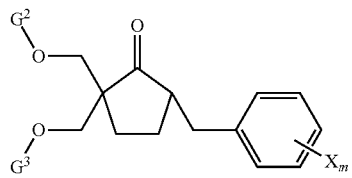

(Ic)

wherein, in general formula (Ic), X, $G^2$, $G^3$, and m are the same as X, $G^2$, $G^3$, and m in general formula (IIc) above, respectively.

8. The method of producing a carbonyl compound according to claim 7, wherein the compound represented by general formula (IIc) above is a compound represented by general formula (IId) below; and the carbonyl compound represented by general formula (Ic) above is a carbonyl compound represented by general formula (Id) below:

[Formula 9]

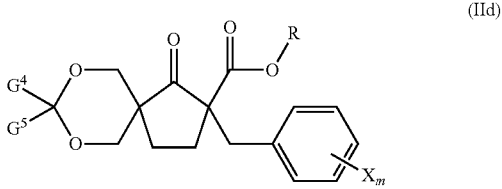

(IId)

wherein, in general formula (IId), $G^4$ and $G^5$ each independently represent a hydrogen atom, an alkyl group having from 1 to 4 carbons, an alkenyl group having from 1 to 4 carbons, a substituted or unsubstituted phenyl group, naphthyl group, or benzyl group, $G^4$ and $G^5$ may be bonded to each other and, together with a carbon atom to which $G^4$ and $G^5$ are bonded, form a ring; and R, X, and m are the same as R, X, and m in general formula (IIa) above, respectively; and

[Formula 10]

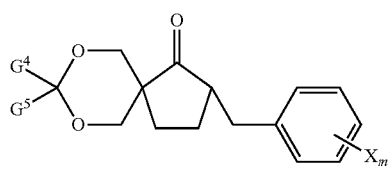

(Id)

wherein, in general formula (Id), X, $G^4$, $G^5$, and m are the same as X, $G^4$, $G^5$, and m in general formula (IId) above, respectively.

9. The method of producing a carbonyl compound according to claim 8, wherein $G^4$ and $G^5$ are each independently a hydrogen atom or an alkyl group having from 1 to 4 carbons.

10. The method of producing a carbonyl compound according to claim 7, further comprising a step of: adding a tertiary amine in the reaction system.

11. The method of producing a carbonyl compound according to claim 5, wherein m is an integer from 0 to 2; and when m is 1 or 2, X is a halogen atom.

* * * * *